(12) United States Patent
Lantis et al.

(10) Patent No.: US 8,292,100 B2
(45) Date of Patent: Oct. 23, 2012

(54) METHOD AND APPARATUS FOR SOLAR-BASED WATER DISINFECTION

(75) Inventors: Robert Lantis, Weaverville, NC (US); Joesph Patrick Phelan, Taringa (AU); Anna Phelan, Taringa (AU)

(73) Assignee: Aquasolix Corporation, Baldwin, NY (US)

( * ) Notice: Subject to any disclaimer, the term of this patent is extended or adjusted under 35 U.S.C. 154(b) by 0 days.

(21) Appl. No.: 13/108,523

(22) Filed: May 16, 2011

(65) Prior Publication Data

US 2011/0215054 A1    Sep. 8, 2011

Related U.S. Application Data

(60) Provisional application No. 61/345,064, filed on May 14, 2010.

(51) Int. Cl.
C02F 1/32 (2006.01)
C02F 1/00 (2006.01)

(52) U.S. Cl. .............. 215/45; 215/40; 215/44; 215/316; 215/365; 210/748.01; 210/748.1; 210/91; 422/186.3; 422/186; 422/21; 422/24; 250/432 R; 250/438; 206/459.5; 235/487; 235/488

(58) Field of Classification Search ............... 210/91, 210/742, 151, 149, 85, 748.14, 743; 422/21, 422/22, 24, 186, 186.3; 215/40, 45, 44, 316, 215/365; 222/23; 206/459.5; 977/773, 903

See application file for complete search history.

(56) References Cited

U.S. PATENT DOCUMENTS

| | | | |
|---|---|---|---|
| 4,610,298 A | 9/1986 | van Schagen et al. | |
| 4,788,433 A | 11/1988 | Wright | |
| 4,829,187 A | 5/1989 | Tomita et al. | |
| 4,988,484 A | 1/1991 | Karlson | |
| 5,053,110 A | 10/1991 | Deutsch | |
| 5,085,753 A | 2/1992 | Sherman | |
| 5,181,991 A | 1/1993 | Deutsch | |
| 5,192,424 A * | 3/1993 | Beyne et al. ................ | 210/85 |
| 5,281,310 A | 1/1994 | Djelouah et al. | |
| 5,436,115 A | 7/1995 | Mullis | |
| 5,581,090 A | 12/1996 | Goudjil | |
| 5,790,725 A | 8/1998 | Rykowski et al. | |
| 5,839,078 A | 11/1998 | Jennings et al. | |

(Continued)

FOREIGN PATENT DOCUMENTS

CN    2553305 Y    5/2003

(Continued)

OTHER PUBLICATIONS

Berney, M., Weilenmann, H.-U., Ihssen, J., Bassin, C., Egli, T. (2006). Specific growth rate determines the sensitivity of enteric bacteria to thermal, UVA and solar disinfection. Applied and Environmental Microbiology, 72(4), 2586-2593.

(Continued)

Primary Examiner — Joseph Drodge
Assistant Examiner — Cameron J Allen
(74) Attorney, Agent, or Firm — Gianna Julian-Arnold; Saul Ewing LLP

(57) ABSTRACT

A highly portable solar UV disinfection and water storage container with a uniquely traceable security seal that passively indicates by means of a permanent photochromic color change the efficacy of the UV disinfection process performed upon the drinking water within the sealed container.

16 Claims, 9 Drawing Sheets

U.S. PATENT DOCUMENTS

| | | | |
|---|---|---|---|
| 5,862,277 | A | 1/1999 | Riser et al. |
| 6,090,296 | A | 7/2000 | Oster |
| 6,433,035 | B1 | 8/2002 | Grinevich et al. |
| 6,475,433 | B2 | 11/2002 | McGeorge et al. |
| 6,504,161 | B1 | 1/2003 | Jackson et al. |
| 6,633,042 | B1 | 10/2003 | Funken et al. |
| 6,652,638 | B2 | 11/2003 | Fox et al. |
| 6,689,438 | B2 | 2/2004 | Kennedy et al. |
| 6,734,440 | B2 | 5/2004 | Questel et al. |
| 6,806,022 | B1 | 10/2004 | Kawabe et al. |
| 7,476,874 | B2 | 1/2009 | Patel |
| 7,589,331 | B2 | 9/2009 | Havens et al. |
| 7,642,303 | B2 | 1/2010 | Shakely et al. |
| 7,837,865 | B2 | 11/2010 | Wadstrom |
| 2001/0019110 | A1 | 9/2001 | Faran et al. |
| 2007/0221362 | A1 | 9/2007 | Stewart et al. |
| 2009/0078669 | A1* | 3/2009 | Sakaguchi et al. .......... 215/45 |
| 2010/0155339 | A1 | 6/2010 | Gunter |

FOREIGN PATENT DOCUMENTS

| | | |
|---|---|---|
| DE | 4120340 A1 | 12/1992 |
| GB | 2040436 A | 8/1980 |
| WO | 98/05594 | 2/1998 |
| WO | 01/28933 A1 | 4/2001 |
| WO | 02/066905 A2 | 8/2002 |

OTHER PUBLICATIONS

Graf, J., Togouet, S. Z., Kemka, N., Nyiytegeka, D., Meierhofer, R., Pieboji, J. G. (2010). Health gains from solar water disinfection (SODIS): evaluation of a water quality intervention in Yaoundé, Cameroon. Journal of Water and Health, 08.4, 779-796.

Gurung, P., Grimm, B., & Autenrieth, M. (2009). Disseminating the SODIS method: Which approach is most effective? Waterlines, 28(2),130-143(14).

King, B. J., Hoefel, D., Daminato, D. P., Fanok, S., & Monis, P. T. (2008). Solar UV reduces *Cryptosporidium parvum* oocyst infectivity in environmental waters. Journal of Applied Microbiology, 104(5), 1311-1323.

McGuigan, K. G., Mendez-Hermida, F., Castro-Hermida, J. A., Ares-Mazas, E., Kehoe, S. C., Boyle, M., et al. (2006). Batch solar disinfection inactivates oocysts of *Cryptosporidium parvum* and cysts of *Giardia muris* in drinking water. Journal of Applied Microbiology, 101(2), 453-463.

Reed, R. H., Mani, S. K., Meyer, V. (2000). Solar photo-oxidative disinfection of drinking water: preliminary field observations. Letters in Applied Microbiology, 30(6), 432-436.

Schmid, P., Kohler, M., Meierhofer, R., Luzi, S., & Wegelin, M. (2008). Does the reuse of Pet bottles during solar water disinfection pose a health risk due to the migration of plasticisers and other chemicals into the water? Water Research, 42(20), 5054-5060.

Wegelin, M., Canonica, S., Alder, A. C., Marazuela, D., Suter, M. J. F., Bucheli, T. D., et al. (2001). Does sunlight change the material and content of polyethylene terephthalate (PET) bottles? Journal of Water Supply Research and Technology-Aqua, 50(3), 125-133.

Wegelin, M., Canonica, S., Mechsner, K., Fleischmann, T., Pesaro, F., & Metzler, A. (1994). Solar water disinfection: Scope of the process and analysis of radiation experiments. Journal of Water Supply: Research and Technology—Aqua, 43(4), 154-169.

* cited by examiner

METHOD AND APPARATUS FOR SOLAR-BASED WATER DISINFECTION

CROSS-REFERENCE TO RELATED APPLICATIONS

This application claims priority to the U.S. provisional application 61/345,064 filed on May 14, 2010, the contents of which are incorporated in its entirety.

FIELD OF THE INVENTION

The present invention relates to solar-based disinfection of water-borne pathogens. Specifically, the present invention relates to methods and designs that produce a consistent and fool-proof process, as well as a fail-safe indication of both disinfection efficacy and physical security condition of the sealed drinking water container.

BACKGROUND OF THE INVENTION

Each year millions of humans die from water borne pathogens. One statistic quoted by The World Bank, The World Health Organization, and the Harvard School of Public Health, among others, is that 1.8 million children die each year from simple, preventable cases of diarrhea which are caused by drinking water contaminated with pathogens. The human toll equates to over 200 children's lives lost per hour, and nearly 5,000 per day. This is mostly an issue within the developing regions, but also can become an issue in industrialized nations in times of war, or natural disasters such as floods, earthquakes, tsunamis, or any time civil unrest or terrorism disrupts centrally distributed and disinfected tap water, whose systems often rely heavily on chemicals and electric power.

It is known that direct solar radiation is one energy source that is capable of disinfecting water. There are numerous methods and devices for direct solar-based water disinfection; these usually utilize one or more bands of naturally-occurring radiation comprised of thermal (infrared), visible, and/or ultraviolet light energy. The thermal disinfection mechanism is characterized by sufficiently heating the water for some minimum duration and at some minimum temperature to induce pasteurization of the water. The non-thermal disinfection mechanism is characterized by sufficiently exposing the DNA and/or RNA of micro-organisms to photon energies that can impart direct dissociation of the chemical compounds that are the "building blocks" of the DNA/RNA chain, thereby breaking the cellular replication cycle and continued growth of the organism. While it is possible to perform disinfection with large amounts of visible light photons, the increasingly higher photon energy of shorter wavelength ultraviolet light photons produces much greater disinfection in terms of pathogen log reduction per unit average fluence of light exposure. This is why ultraviolet light within the UV-C band (wavelength ~210 nm to ~290 nm, also known as the "disinfection band") is most efficacious and preferred. However, for the purpose of terrestrial-based direct solar disinfection applications, because only small amounts of UV-C band ultraviolet light passes from the sun to below the upper atmosphere, the non-thermal mechanism is practically limited to the less-energetic photons comprising the UV-A band (wavelengths 320-400 nm) and the UV-B band (wavelengths 290-320 nm). Herein we shall refer collectively to these bands as "broadband UV".

There exists a well-known, simple, very low-cost, and effective solution that can save lives by purifying the water using natural sunlight; this is known as the SODIS (SOlar DISinfection) method. The effectiveness of the SODIS method was first discovered by Professor Aftim Acra at the American University of Beirut in the early 1980s. Additional research was conducted by the research groups of Martin Wegelin at the Swiss Federal Institute of Aquatic Science and Technology (Eawag) and Dr Kevin McGuigan at the Royal College of Surgeons in Ireland. Clinical control trials were pioneered by Professor Ronan Conroy of the RCSI team in collaboration with Dr. T. Michael Elmore Meegan.

A simple explanation of the standard SODIS method is as follows:

1) Fill an ultraviolet-transparent P.E.T. plastic bottle about half to three quarters full of relatively "clear" water. For example, this might require that the water first be pre-filtered with a simple sand filter composed of a layer of gravel, sand, and perhaps charcoal. None-the-less, this water still may contain deadly pathogens.

2) Cap the bottle tightly.

3) Shake the bottle for at least 30 seconds, thereby importantly mixing in some oxygen, and subsequently increasing the oxidizing potential to the water, thus enhancing the efficacy of the available sunlight.

4) Expose the bottle to full sunlight for at least 6 hours. An additional process enhancement is to place the bottle atop a corrugated metal surface, so that some sunlight will be reflected back, thereby creating two passes through the water.

5) The water should then be free of dangerous biological pathogens.

The SODIS method treats the contaminated water through several synergistic mechanisms: radiation in the spectrum of UV-A (as well as a lesser amount of radiation in the UV-B spectrum), increased water temperature, and some limited oxidation from the interaction of ultravioletT with dissolved oxygen. It has been shown that if the water temperature rises to as little as 50° C., the disinfection process is three times faster than otherwise achievable without the thermal enhancement mechanism.

There are, however, several problems and short-comings with the SODIS method of water disinfection. There is no effective way to positively validate that the water contained in a bottle treated by the SODIS method has indeed been disinfected. There is no appropriate feedback mechanism, safety/security seal, or quality control of any kind. Many people may be suspicious of lower technology solutions. As a result, they will not use the water for any means, preferring to spend scarce third world income on bottled water, even if that sealed bottle represents more than a day's wage. This means that in many cases, unfortunate parents make an agonizing choice between guaranteeing their family's health by spending their limited income on expensive bottled water, or else incur a potentially life threatening risk by using water from an unreliable source, thereby saving the onerous expense of bottled water.

An additional liability of standard SODIS technology is a side-effect of one of its otherwise advantages: it utilizes used P.E.T. plastic bottles, so encourages re-use while providing an essentially no-cost source of containers. The detrimental side of this, however, is that recent evidence shows that heating plastic-bottled water is a potentially unsafe practice, due to the release from the plastic of cancer-causing and endocrine-disrupting compounds. So, the more immediate life-saving benefits of SODIS water treatment are compromised by the long-term risk effects of chemical poisoning.

A device that provides a limited measure of disinfection process efficacy confirmation is a reusable low-melting temperature wax-based Water Pasteurization Indicator (WAPI), typically costing $5 to $10. Note that this is an entirely thermal energy-based (that is, pasteurization) indicator, and must first be inserted into the bottle prior to pasteurization, then removed by its string tether prior to utilizing the water. Therefore, the combination of expense, complexity, lack of permanent and fail-safe security, and subsequent re-contamination risk is problematic, the WAPI is therefore considered by some to not be a compelling technology that fulfills the requirements for wide-spread implementation.

In order for SODIS-based treatment to realize its full potential and provide less-fortunate families with a simple, yet compelling solution to their potable water needs, there is therefore a need to solve the issues now identified as problematic and adverse to the widespread implementation of SODIS.

Wadstrom (U.S. Pat. No. 7,837,865) discloses a device using a combination of solar heat and ultraviolet, however, there is no ultraviolet disinfection (nor Pasteurization) indication mechanism, nor does is there a means by which a user will know they are in receipt of a securely sealed container.

Funken (U.S. Pat. No. 6,633,042) discloses a solar-based photobioreactor claimed effective for water disinfection, however the photobioreactor is not suitable as a portable container, nor does it provide for a securely sealed container or an indication of disinfection efficacy.

The invention disclosed herein provides the methods and means by which one may benefit from SODIS-type water disinfection that is uniquely and inherently fail-safe, thereby confirming to the user that the bottle contents are secure, safe, and healthful for human consumption. An additional (and complimenting) benefit of this invention is socio-economic in nature, in that it enables the establishment of a wide network of very local, grass-roots-based entrepreneurial endeavors, all based upon the need to create, distribute, sell, and recycle/support the ensuing products. This is a resource that supplies a local solution to a local problem.

SUMMARY OF THE INVENTION

Accordingly, a primary object of the present invention is to provide a verifiable, fail-safe, permanent, and tamper-proof indication of solar-based water ultraviolet purification/disinfection integrity.

A further object of this invention is to provide water bottle designs, methods of manufacturing, and methods of disinfection process that provide an effective means of automatically indicating water disinfection integrity based upon metrology techniques (the science of measurement) that are simply and passively-driven by the solar ultraviolet disinfection process.

A further object of this invention is to incorporate within the method and device a simple, inexpensive means for water bottle/container identification and production/packing lot tracking, thereby enabling process validation capability and reporting structure for regulatory and health & safety departments.

A further object of this invention is to provide an effective and reliable solar-based water disinfection system that is suitable for locally-distributed and managed proprietorships.

These and other objects are achieved in the present invention.

The present invention overcomes the risks and uncertainties caused by the lack of positive visual confirmation of water disinfection integrity, while simultaneously passively providing both the metrology for measuring adequate ultraviolet disinfection, and the secure and tamper-proof indication thereof. Unlike heretofore SODIS systems that utilize unstable and cancer-causing plastic compounds for the bottle and other components, this invention advantageously incorporates no such materials, thereby posing no additional long-term health risks.

The combination of features of the present invention provides a safe and reliable, secure, and cost-effective solar-based water disinfection container design, methods of manufacturing, and methods of disinfection process, thereby creating a compelling resource for enabling widespread implementation of this unique SODIS technology. There has thus been outlined, rather broadly, the more important features of the invention in order that the detailed description thereof that follows may be better understood, and in order that the present contribution to the art may be better appreciated. There are, of course, additional features of the invention that will be described further hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that equivalent constructions insofar as they do not depart from the spirit and scope of the present invention, are included in the present invention.

For a better understanding of the invention, its operating advantages and the specific objects attained by its uses, reference should be had to the accompanying drawings and descriptive matter which illustrate preferred embodiments of the invention.

BRIEF DESCRIPTION OF THE DRAWINGS AND THE FIGURES

DETAILED DESCRIPTION OF THE INVENTION

Figure 1:
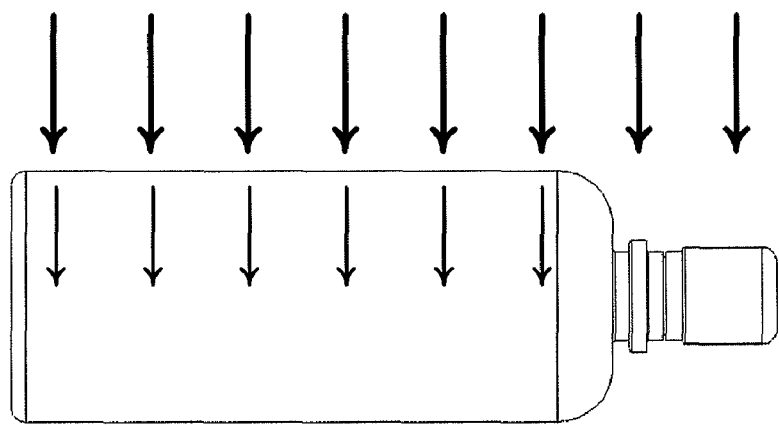
FIG. 1 illustrates a conventional SODIS system container.

FIG. 1 illustrates a conventional plastic bottle left to sun exposure in the prior art of the existing SODIS method. While the method has been proven effective if the criteria of certain conditions are met, a user has no immediate feedback or readily-available practical reliable means to know whether the water thus contained is free of pathogens and safe for drinking.

Figure 2:
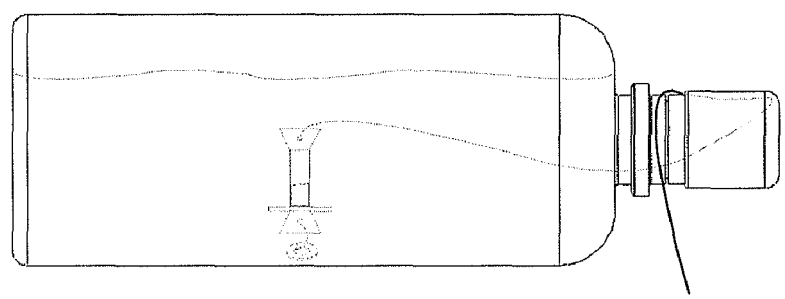
FIG. 2 illustrates a Water Pasteurization Indicator used with SODIS.

FIG. 2 illustrates the existing art of a Water Pasteurization Indicator. Again, there is no fail-safe methodology for insuring that the water thus contained is free of pathogens and safe for drinking. For example, the unit indicates only that at one time some certain minimum temperature was met. There is no fail-safe indication of seal integrity, or if microbes have since been introduced via ambient exposure or by means of the string that exits the bottle.

Figure 3:
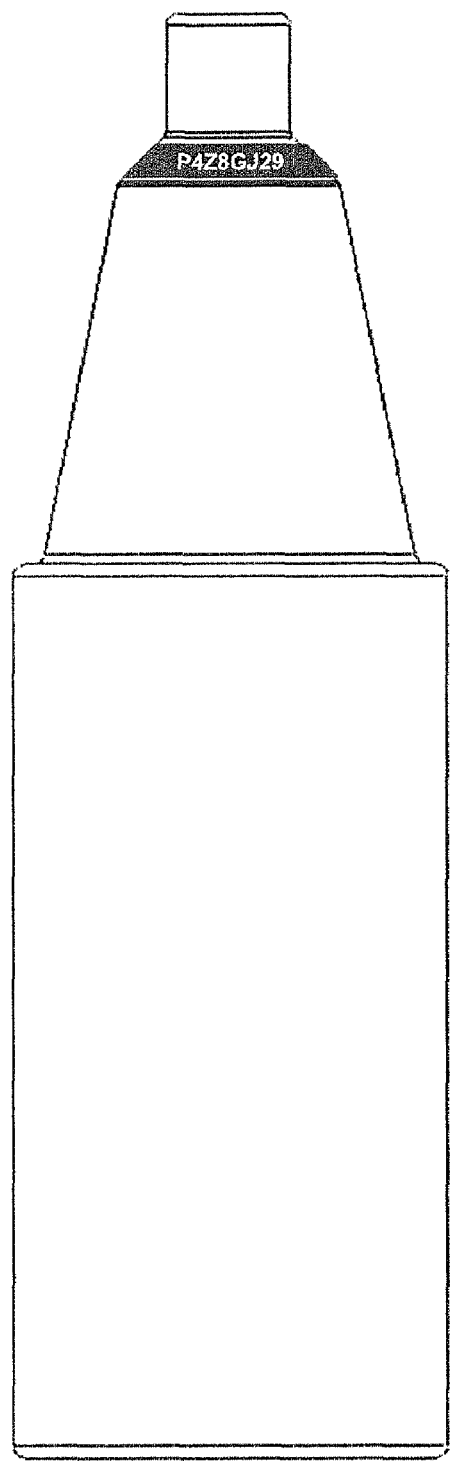
FIG. 3 illustrates an example of a single fail-safe SODIS container with fail safe security seal.

FIG. 3 illustrates an example of a single fail-safe SODIS container with fail-safe security seal located around the base of the cap. This modular bottle style comprises the drinking water product as delivered to a customer. A safety security seal around the base of the cap is the visible means of proving that the water is safe to drink. This security seal is unique because it contains the imprinted serial number in raised (or incuse) lettering of the bottle into which it is fitted, providing a traceable identification number and validation of the bottle's origin, position in the array when treated, the user's identity, location, or any number of useful data points required to guarantee and track the effectiveness of the process.

Figure 4:
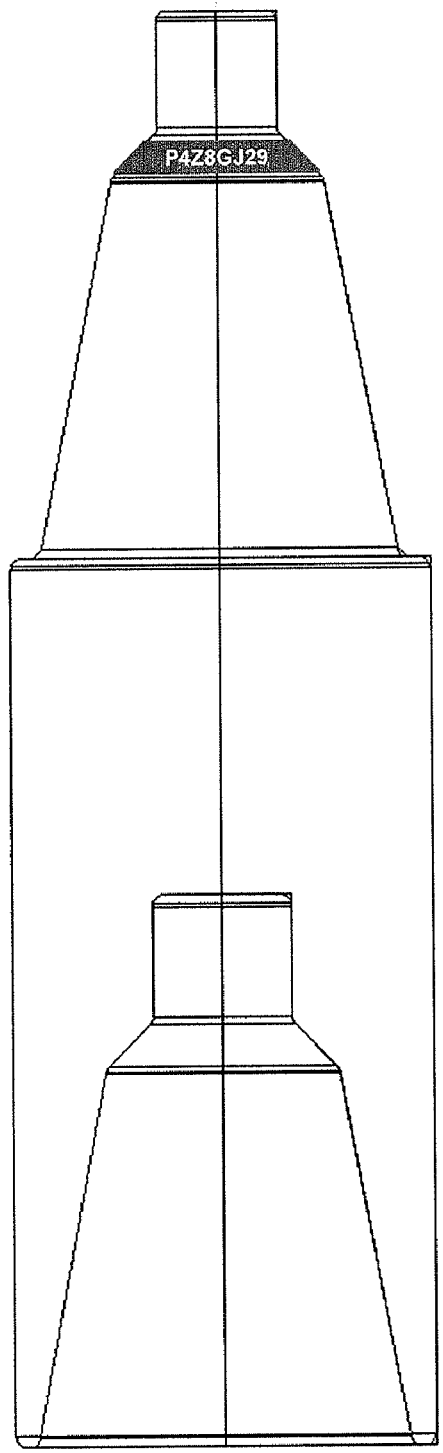
FIG. 4 illustrates an example of a single fail-safe SODIS container with fail safe security seal shown with the container's interior concave bottom which fits to a corresponding container.

FIG. 4 illustrates an example of a single fail-safe SODIS container with fail safe security seal shown with the container's interior concave bottom which fits onto a corresponding identically-shaped container. This modular design feature is necessary to create an array of fitted containers all of which are then exposed simultaneously to the sun's rays, receiving essentially equal ultraviolet fluence and guaranteeing pathogen free water. Within the concave bottle section, a serial number is to be imprinted on the adjoining bottle security seal. This number will be permanently molded or etched in reverse lettering within the concave section.

The security seal can be made from various suitable materials, such as a polymer, a clay-like material, or an adhesive-like sealant that is at first a viscous liquid, somewhat like thick toothpaste in consistency. The security seal material is designed to be cured to the proper hardness and color change upon exposure to the desired integrated fluence of ultraviolet light (i.e., the minimum level that will achieve the desired disinfection efficacy). Numerous ultraviolet and visible light cured resins and other candidate materials exist in the commercial marketplace. This embodiment presumes a ultraviolet cured, flexible plastic or other sealant that creates an adequate security seal upon curing but will not bond the two bottles together. This embodiment also presumes a security seal that cures under conditions that also render the water inside the container suitable for human consumption. The neck of the bottle can contain a series of raised dots, ridges or other textured surface to serve as a preferential site of high surface area for enhanced bonding. When the bottles are separated, this will insure that the security seal remains on the bottle's neck and is not left within the concave interior surface. With the exception of the etched or molded serial number, the interior region which is in contact with the ultraviolet curing plastic should be as smooth as possible to reduce the chance that the plastic preferentially bonds inside the preceding bottle rather than forming a security seal.

Figure 5:
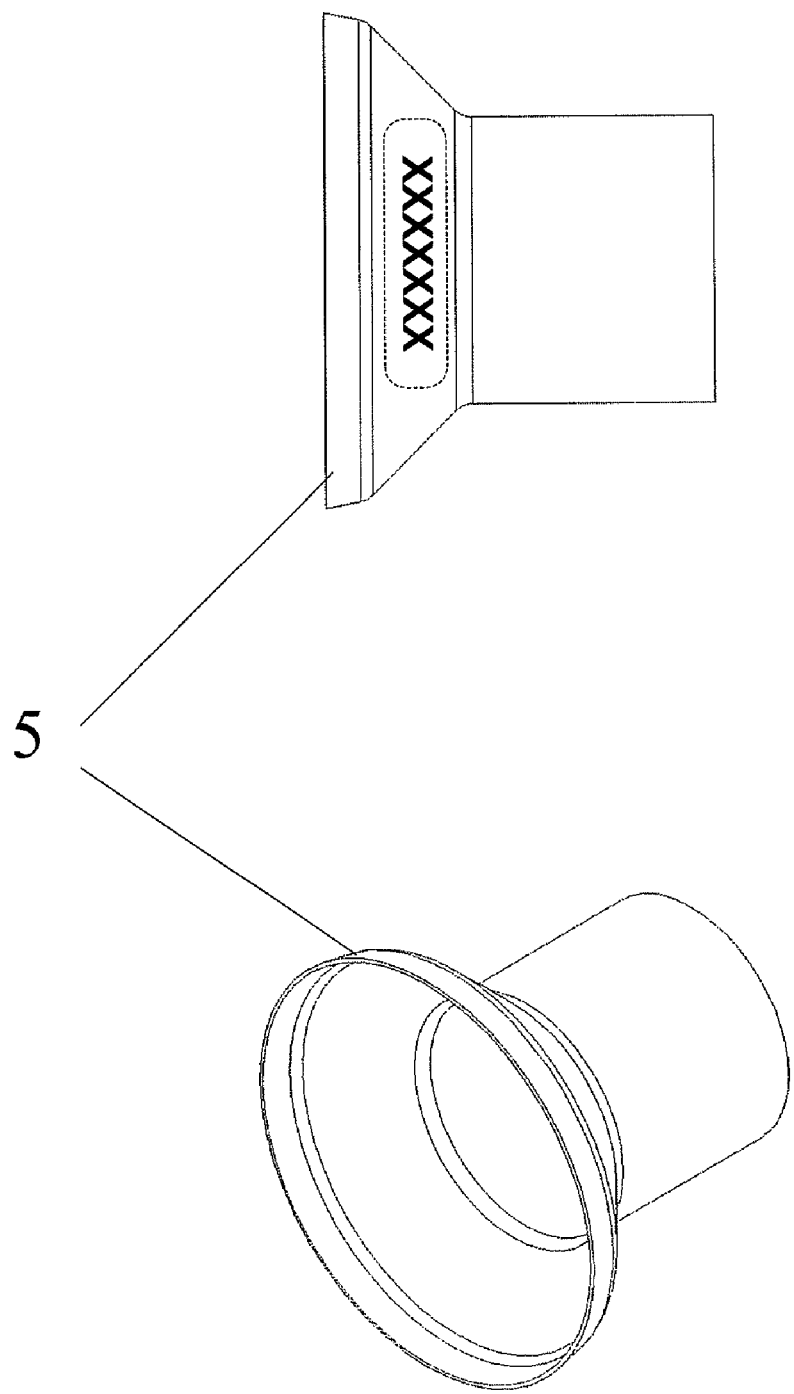
FIG. 5 illustrates an example of a serial number insert that can be permanently set into the interior concave bottom of each water container so that each container can be fabricated from an identical mold.

FIG. 5 illustrates an example of a serial number insert that can be permanently set into the interior concave bottom of each water container so that each container can be fabricated from an identical mold. Because there can be difficulties in molding bottles with unique identifying marks, particularly upon a less accessible interior portion of the concave bottom, this is an alternate method of uniquely serializing each container. This device, indicated by the number "5" in this and subsequent figures, is essentially a "serialized dome" that is permanently affixed within the space intended to accommodate the insertion of the neck and cap section of a mating water container.

Figure 6:
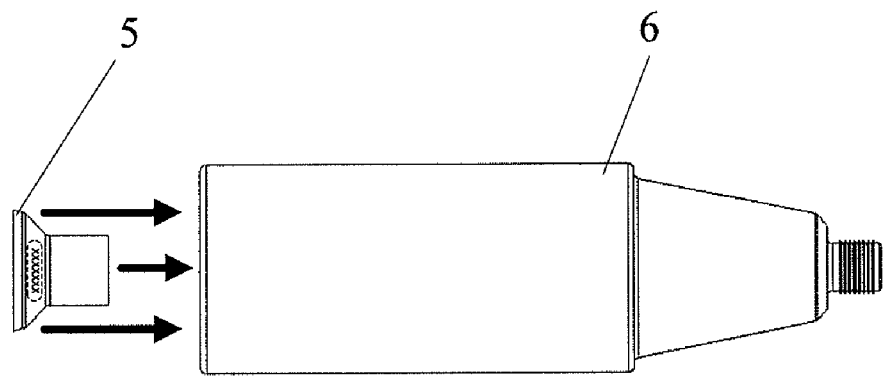
FIG. 6 illustrates how a serial number insert is set into the concave bottom of a water container.
Figure 6:
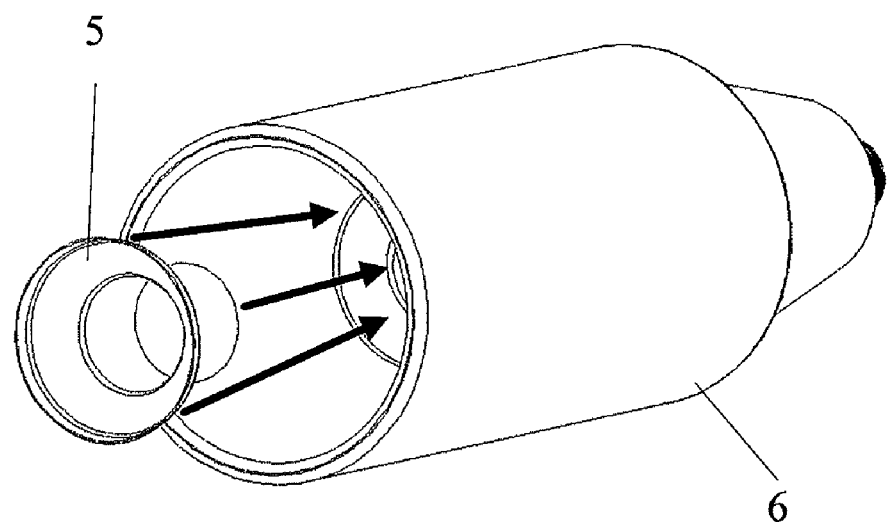

FIG. 6 illustrates how a serial number insert is set into the concave bottom of a water container. Various methods of permanent fixation, such as a force-fit, or adhesive, can be utilized.

Figure 7:
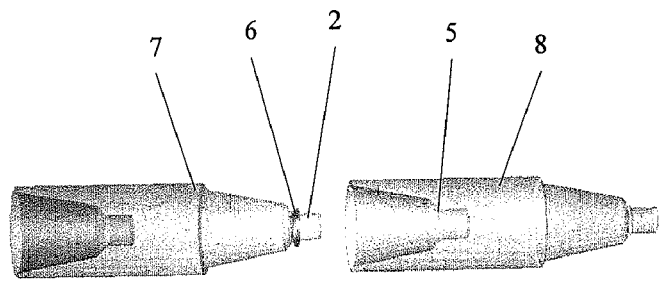
FIG. 7 illustrates two nested fail-safe SODIS containers, with a means for installing a fail-safe SODIS indicating security seal.
Figure 7:
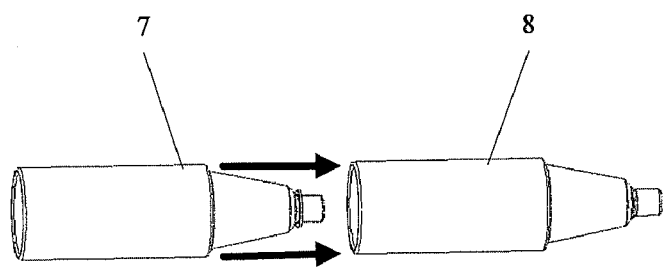
Figure 7:
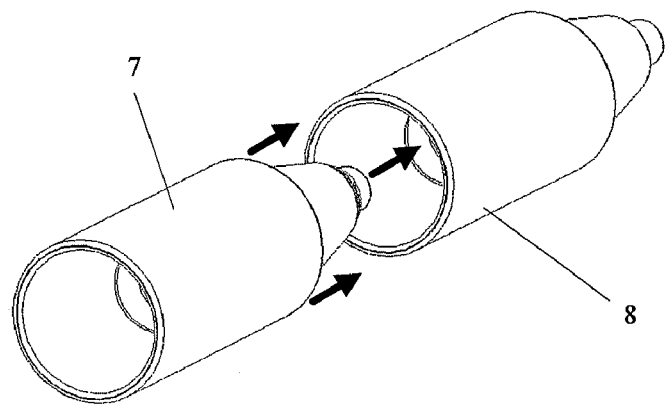

FIG. 7 illustrates two nestable fail-safe SODIS containers, with a means for installing a fail-safe SODIS indicating security seal. The numbered components in this figure are as follows: item 2 represents the screw cap on the bottle, item 5 represents the interior, concave section of the preceding bottle item 8 on which a serial number insert is etched or molded, item 6 represents the uncured and yet un-impressed ring of material that will be pressed and ultraviolet cured to become the serial numbered plastic resin security seal on the next bottle, and item 7 represents the next bottle. As bottle 7 is inserted into the concave portion of bottle 8, the uncured and moldable ring 6 is pressed into an uncured security seal that is imprinted with the serial number upon the mating interior 5 section of bottle 8. This modular bottle design with fitted, imprinted serial numbers can be further duplicated and stacked into a large horizontal array of stacked bottles.

Figure 8:
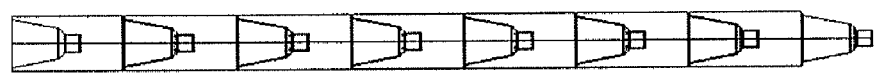
FIG. 8 illustrates a series of nested fail-safe SODIS containers.
Figure 8:
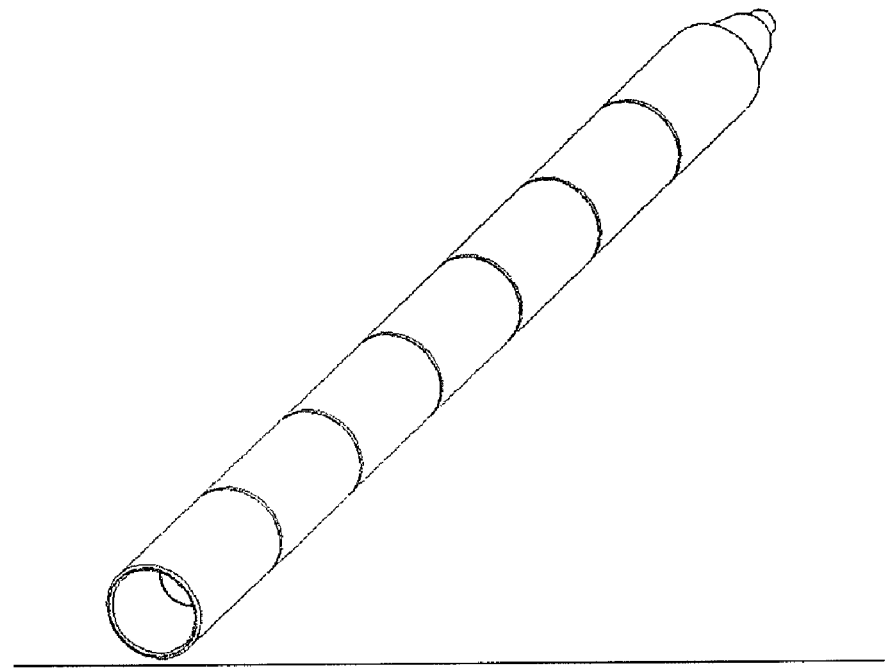

FIG. 8 illustrates an example of a series of nested fail-safe SODIS containers. Note that in this example, the last bottle has an open-ended concave bottom without a mating bottle inserted into the open volume. This open-ended section can accommodate the insertion of a special end cap as shown in FIG. 9.

Figure 9:
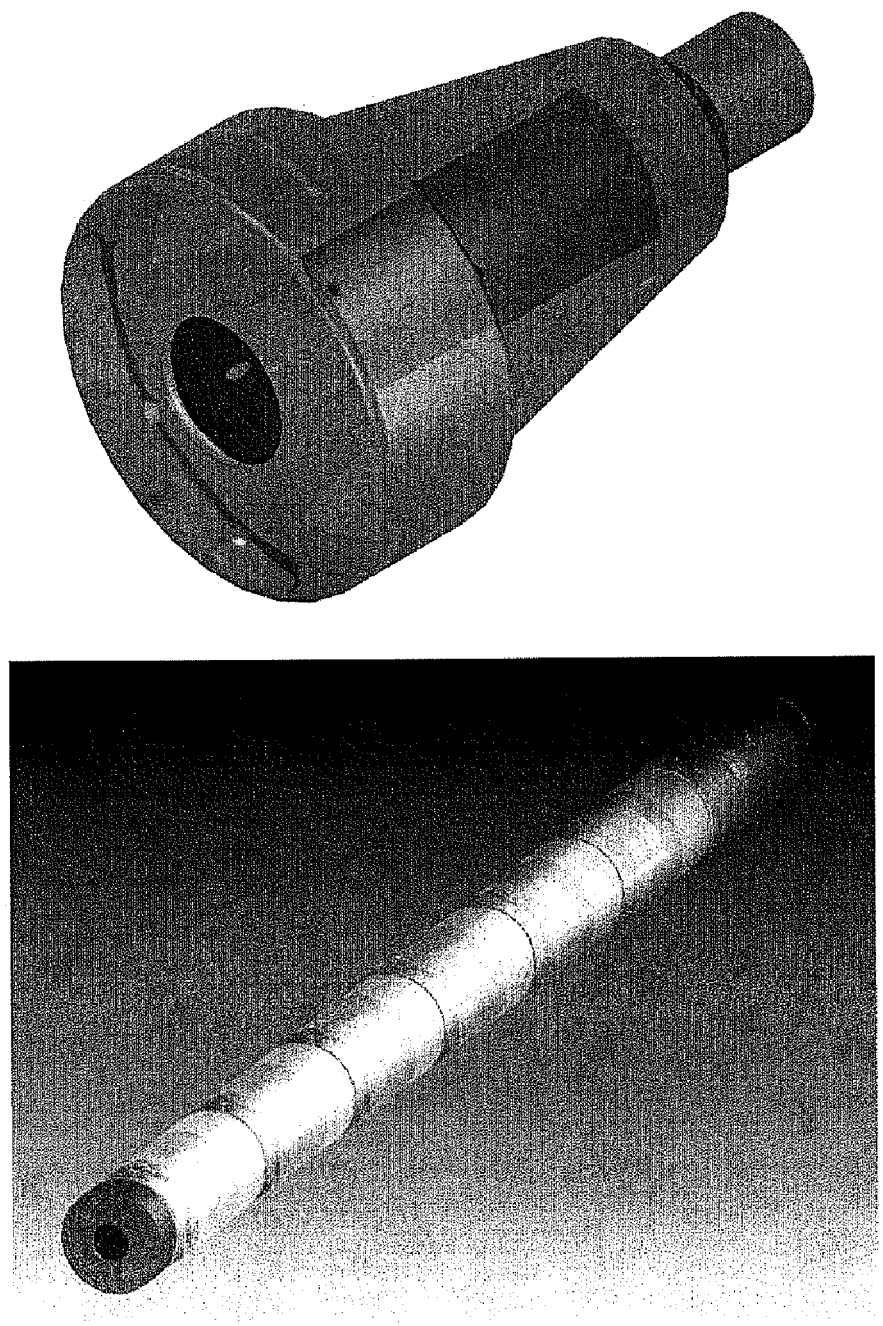
FIG. 9 illustrates a means for passively measuring average ultraviolet fluence on the last container of a horizontal row.

FIG. 9 illustrates a means for passively measuring average ultraviolet fluence exposure upon the last container of a horizontal row. This device is essentially an "end cap" that is fitted into the last bottle. This end cap will experience the identical ultraviolet fluence as the security seal on the caps for each bottle in the array that precedes it. Similar to the actual water containers, an uncured ring (item 6 in FIG. 7) of ultraviolet curable sealing material is placed around what would otherwise be the neck and cap region. The last bottle on the open end of a horizontal array of bottles would contain this passive measurement end cap during the SODIS process, and then the security seal would stay with the operator (i.e., the packer/supplier entity) as a permanent record of the array's ultraviolet fluence as experienced during the curing of the security seals. In practice, since this end cap serialized security seal is a passive proxy for ultraviolet fluence and should be inexpensive, one could devise an operational protocol whereby these security seals are preserved as a permanent record of the ultraviolet fluence intercepted by the array and available for disinfection. It would also be imprinted with a serial number from the preceding bottle (6), and form a permanent and auditable record of the ultraviolet fluence experience by the bottle array once treated, irrespective of where the treated bottles were shipped. In an alternative embodiment, the end cap is an electronic device that more actively measures ultraviolet influence. Such a device could be battery or solar powered for example.

Figure 10:
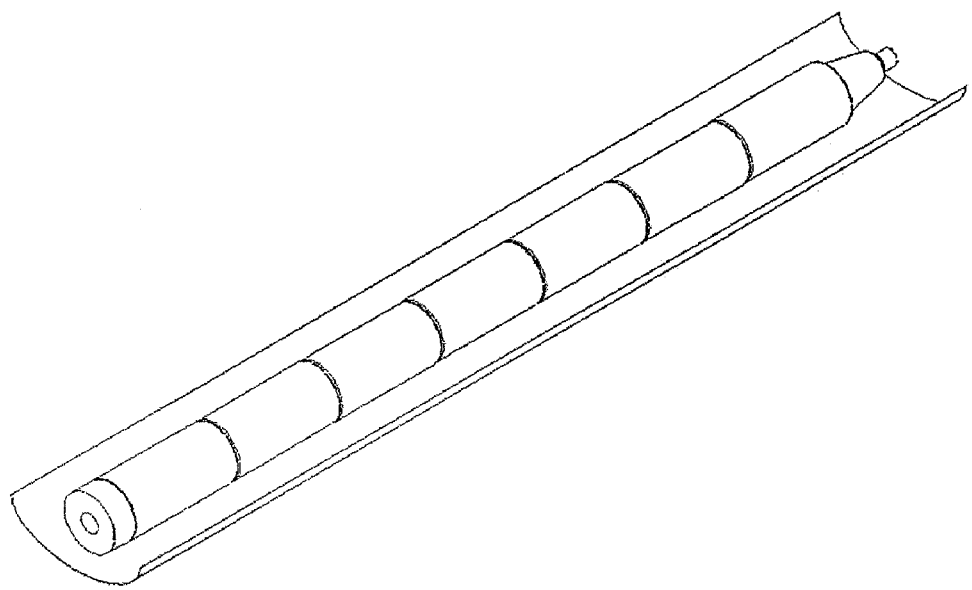
FIG. 10 illustrates a parabolic reflector-based SODIS enhancement.

FIG. 10 illustrates a parabolic reflector-based SODIS enhancement. By positioning the array in the focus of a parabolic mirror, the normal 6 hour conventional SODIS time required can be reduced substantially. For example, various forms of preferential/selective infrared band filters/reflectors may be employed. It is contemplated that such design features ensure that the array does not withstand excessive thermal stress.

Alternative means of quality control and/or quality assurance include integration of existing technologies such as identification microdots and color changing plastic. Identification microdots comprise a plethora of tiny numbered and identical tags, as small as sand. These dots can provide a specific ID for the user and be imbedded in or upon the cap security seal material without compromising the ultraviolet curable material's performance. Identification microdots would provide yet another level of auditable tracking ability to identify the specific user who placed the uncured plastic on the bottle array.

The color changing plastic can provide a visual indicator that water is safe to drink. If the security seal material changes color when cured by the sufficient ultraviolet fluence, this provides the operator with a visible means of knowing that the process is complete and the bottles are suitable for delivery, sale, or other conveyance with full confidence that sufficient ultraviolet disinfection fluence was applied to the array of bottles.

There are various methods known in the art for indicating ultraviolet exposure by means of color changes in materials, as well as a diverse range of applications for such technology. Exemplary writings related to such color change technology include: Mullis (U.S. Pat. No. 5,436,115) discloses a human sunlight-exposure specific ultraviolet sensitive indicating system for use on skin and/or as a personal ultraviolet dosimetry device; Questal (U.S. Pat. No. 6,734,440) discloses a similar human sunlight-exposure specific ultraviolet sensitive indicating system for use on skin, but utilizes different compounds and extends the ultraviolet sensitivity to a spectrum between 230 nm and 365 nm; Goudjil (U.S. Pat. No. 5,581,090) discloses an ultraviolet detector based on a photochromic composition that changes color upon exposure to ultraviolet rays, the photochromic material is dissolved in a solvent and applied to an article such as a watch or credit card. However, the color change in these prior art disclosures is reversible. The present invention requires a non-reversible photochromic conversion in order to permanently indicate cumulative broadband ultraviolet exposure.

Further examples include McGeorge (U.S. Pat. No. 6,475,433) which discloses a cumulative UV-C sensitive indicating strip that outputs relative UV-C dosage received from mercury lamps (254 nm) by means color gradations compared against a reference chart; Havens (U.S. Pat. No. 7,589,331) discloses a cumulative UV-C sensitive material that can be set to photochromically react at some specifically-chosen level of UV-C fluence. Products based upon this and other similar photochromic techniques are commercially available, as are also similar technologies that advantageously extend the color change response characteristics into the UV-A and UV-B bands. Such commercially available ultraviolet exposure color change indicators are readily adaptable for incorporation into the cap seal material of this invention.

Therefore in alternative embodiments a water disinfection and containment system is disclosed herein. In varying embodiments the security seal is a material that cures under ultraviolet light. Exemplary materials include polymer, wax and clay. The security seal provides a permanent visual indication of the sufficient exposure level (or dose) of integrated broadband ultraviolet fluence. In one embodiment the ultraviolet fluence is 210 nm to 400 nm. The security seal thereby provides feedback as to disinfection efficacy that is achieved within the water storage container. In one embodiment there is an ultraviolet-induced color change in the cap security seal material. In an alternative embodiment, there are a plurality of containers and integrity of purification reference is obtained from a corresponding end cap security seal. This end cap security seal can be stored locally by the originating packer/supplier of disinfected water storage containers.

Identity tracking of the originating packer/supplier of disinfected water storage container can be monitored via the inclusion of identification microdots or similar traceable means of monitoring the packer/supplier who performed the packaging of the disinfected water storage container. Identity tracking can also be provided by the use of unique and traceable serial numbers for each storage container.

Stacking of the containers can be facilitated through modifications in shape. As disclosed herein, the neck of one container can be inserted and nested within the base region of any other identical container. Further, the interface surfaces between said nested containers provide a means for stacking multiple containers into an aligned group of containers that may be supported entirely from the two opposing ends of the group. Upon mating of the nested containers, the interface surfaces between said nested containers provide a means for compressing and molding (within the circumferential region between and around the neck and the container's removable cap) an uncured ring of flexible and/or viscous liquid sealing material. When in said nested configuration, the cap security seal material can be exposed to any and all broadband ultraviolet disinfection light that necessarily must first propagate through two container walls and water therein, thereby ensuring that the accumulated ultraviolet upon the sealing ring material represents an attenuated amount that is conservatively less than the accumulated ultraviolet dose exposure within the always lesser-attenuated volume of water within the container Prior to exposure to ultraviolet light (curing) the ultraviolet light cured security seal can be imprinted from either a uniquely identifiable serialized dome inserted inside the accommodating concave base region, or alternately from an uniquely identifiable serialized molding directly located upon the accommodating concave base region of the preceding container, thereby enabling provision of a data tracking mechanism that can link the container array's collective disinfection efficacy to an end cap that serves as a proxy for the array of water containers that are filled, sealed, and disinfected simultaneously.

An end cap can provide passive proxy of sufficient integrated ultraviolet fluence exposure (and, thereby, disinfection efficacy). This end cap can be stored by the originating packer/supplier of disinfected water storage containers for later auditing by regulatory and health care agencies.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention and any equivalent thereto. It can be appreciated that variations to the present invention would be readily apparent to those skilled in the art, and the present invention is intended to include those alternatives. Further, since numerous modifications will readily occur to those skilled in the art, it is not desired to limit the invention to the exact construction and operation illustrated and described, and accordingly, all suitable modifications and equivalents may be resorted to, falling within the scope of the invention.

What is claimed is:

1. A water storage and disinfection container comprising:
   a first container, wherein said container is transparent to ultra violet light, said container having a top and a bottom, wherein said top of said container is narrower than said bottom, said narrowing forming a neck, said bottom comprising a concave or hollowed inward shape corresponding to said top;
   a cap, said cap comprising a internal threaded screw-on tightening and sealing feature, said cap being attachable to said neck;
   a cap security seal, said cap security seal being manually affixed around the base of the cap and the neck, and comprising a material that cures in response to ultraviolet light fluence, wherein said cap security seal is flexible in an uncured state and rigid in a cured state; and
   an ultraviolet light transparent insert comprising serialized identification characters embossed in relief upon a concave or hollowed inward shape surface of said insert, wherein said concave surface or hollowed inward shape of said insert corresponds to said top and said cap when said cap is attached to said neck of said container, wherein said insert is affixed to the concave bottom of said container.

2. The water storage and disinfection container of claim 1, said cap security seal material comprising a polymer, wax, clay-like, or viscous paste-like consistency adhesive material.

3. The water storage and disinfection container of claim 1, wherein said cap security seal is a first color in said uncured state and a second color in said cured state.

4. The water storage and disinfection container of claim 1, wherein said cap security seal cures under ultraviolet fluence conditions sufficient to disinfect the water inside said container.

5. The water storage and disinfection container of claim 4, wherein said cap security seal cures by exposure to the desired integrated fluence level of broadband solar ultraviolet light spectrum from about 210 nm to about 400 nm.

6. The water storage and disinfection container of claim 4, said cap security seal further comprising a unique and traceable serial number specific to each storage container.

7. The water storage and disinfection container of claim 4, further comprising a traceable identification means for identifying the container.

8. The water storage and disinfection container of claim 7, wherein said traceable identification means comprises unique serialized identification characters embossed in relief upon the bottom concave surface.

9. The water storage and disinfection container of claim 4, further comprising a second container, said second container being shaped substantially similarly to said first container, wherein said top of said first container can nest in said bottom of said second container, thereby compressing, molding into shape, and imprinting the uncured cap security seal with the identification characters embossed upon said insert affixed to said second container.

10. A water storage and disinfection container system comprising:
    a plurality of containers, each said container being transparent to ultraviolet light, each said container having a top and a bottom, wherein said top of said container is narrower than said bottom, said narrowing forming a neck, said bottom comprising a concave or hollowed inward shape corresponding to said top;
    a cap, said cap comprising an internal threaded screw-on tightening and sealing feature, said cap being attachable to said neck;
    a cap security seal, said cap security seal being manually affixed around the base of the cap and the neck, and comprising a material that cures in response to ultraviolet light fluence, wherein said cap security seal is flexible in an uncured state and rigid in a cured state;
    an ultraviolet light transparent insert comprising serialized identification characters embossed in relief upon a concave or hollowed inward shape surface of said insert, wherein said concave surface or hollowed inward shape of said insert corresponds to said top and said cap when said cap is attached to said neck of said container, wherein said insert is affixed to the concave bottom of said container;
    an end cap, wherein said end cap is placed upon said top of a first container of said plurality of containers, wherein said end cap is shaped to conform to said top of said first container, said end cap further comprising an insert, said insert being affixed into a bottom cavity of said end cap and comprising embossed identification characters;
    a proxy end cap, wherein said proxy end cap is placed into said bottom of a last container said proxy end cap shaped substantially similarly to said end cap and comprising a proxy cap security seal similar to said security seal, wherein said proxy security seal is manually placed around said proxy end cap; and
    each said container nested with another, top into bottom cavity.

11. The water storage and disinfection method of claim 10, wherein all of said cap security seals are a first color in said uncured state and a second color in said cured state.

12. The water storage and disinfection method of claim 10, wherein said cap security seals cure under ultraviolet fluence conditions sufficient to disinfect the water inside said containers.

13. The water storage and disinfection method claim 10, wherein said cap security seals cure by exposure to the desired integrated fluence level of broadband solar ultraviolet light spectrum from about 210 nm to about 400 nm.

14. The water storage and disinfection method of claim 10, said cap seals further comprising a group of unique and traceable serial numbers specific to said plurality of containers.

15. The water storage and disinfection method of claim 10, further comprising a traceable identification means for identifying each of the plurality of containers.

16. The water storage and disinfection method of claim 15, wherein said traceable identification means comprises unique serialized identification characters embossed in relief upon the bottom of all mating concave surfaces.

* * * * *